(12) United States Patent
Lin et al.

(10) Patent No.: US 6,649,772 B2
(45) Date of Patent: Nov. 18, 2003

(54) 3,6,9-TRISUBSTITUTED CARBAZOLES FOR LIGHT EMITTING DIODES

(75) Inventors: Jiann T'Suen Lin, Taipei (TW); K. R. Justin Thomas, Vellalanvilia (IN); Yu-Tai Tao, Taipei (TW); Chung-Wen Ko, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/990,576

(22) Filed: Nov. 21, 2001

(65) Prior Publication Data

US 2002/0107405 A1 Aug. 8, 2002

Related U.S. Application Data

(60) Provisional application No. 60/252,804, filed on Nov. 22, 2000.

(51) Int. Cl.[7] .............................................. C07D 209/82
(52) U.S. Cl. .......................................... 548/439; 430/59
(58) Field of Search ............................ 548/439; 430/59

(56) References Cited

U.S. PATENT DOCUMENTS 5,422,210 A * 6/1995 Maruyama et al. ............ 430/59

FOREIGN PATENT DOCUMENTS

| DE | 198 31 427 A1 | 7/1998 | ......... C07D/487/04 |
|---|---|---|---|
| JP | 02-183259 | * 7/1990 | |
| JP | 05-140289 | * 6/1993 | |

OTHER PUBLICATIONS

Tang, et al. *Electroluminescence of doped organic thin films.* J. Appl. Phys. vol. 65, No. 9, May 1, 1989, pp. 3610–3616.

Thomas, et al. *Light–Emitting Carbazole Derivatives: Potential Electroluminescent Materials.* J. Am. Chem. Soc., vol. 123, 2001, pp. 9404–9411.

Hartwig, et al. *Room–Temperature Palladium–Catalyzed Amination of Aryl Bromides and Chlorides and Extended Scope of Aromatic C–N Bond Formation with a Commercial Ligand.* J. Org. Chem., vol. 64, 1999, pp. 5575–5580.

Zhu, et al. *Synthesis and Characterization of Monodendrons Based on 9–Phenylcarbazole.* J. Org. Chem., vol. 65, 2000, pp. 116–123.

Nishiyama, et al. *Synthesis of N–Arylpiperazines from Aryl Halides and Piperazine under a Palladium Tri–tert–butylphosphine Catalyst.* Tetrahedron Letters, vol. 39, 1998, pp. 617–620.

* cited by examiner

Primary Examiner—Joseph K. McKane
Assistant Examiner—Kamal Saeed
(74) Attorney, Agent, or Firm—Fish & Richardson P.C.

(57) ABSTRACT

The present invention features substituted carbazole compounds of formula (I):

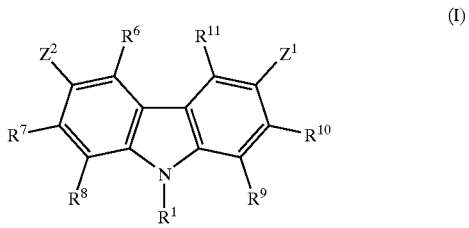

Each of $Z^1$ and $Z^2$, independently, is

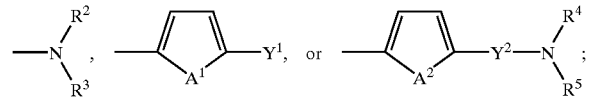

each of $A^1$ and $A^2$, independently, is S, O, NR, or CH=CH; each of $Y^1$ and $Y^2$, independently, is aryl or heteroaryl; each of $R^1$–$R^5$, independently, is aryl or heteroaryl; and each of $R^6$–$R^{11}$, independently, is H, CN, alkyl, OR, NRR', COR, or C(O)OR; and each of R and R', independently, is H or alkyl. The compounds are useful as hole-transporting, light-emitting molecules with high glass transition temperatures.

9 Claims, No Drawings

3,6,9-TRISUBSTITUTED CARBAZOLES FOR LIGHT EMITTING DIODES

RELATED APPLICATIONS

This application claims priority to U.S. provisional application No. 60/252,804, filed on Nov. 22, 2000, the contents of which are incorporated herein by reference.

BACKGROUND

Electroluminescent (EL) devices based on organic thin layers have recently attracted much attention because of their potential uses in large-area flat-panel displays and light-emitting diodes (LED). Organic LEDs have been made with both low molecular-weight organic materials and with polymers. The performance of these devices is significantly influenced by the charge balance between electrons and holes from opposite electrodes. The charge can be balanced by using a bilayer structure including a hole transporting layer and an electron transporting layer. One or both of these layers can be luminescent.

An important quality of organic EL materials is their durability, i.e., thermal and morphological stability. Thus, it is desirable that organic EL materials are not only light-emitting and hole-transporting, but also robust.

SUMMARY

This invention relates to substituted carbazole compounds, which are hole-transporting, light-emitting molecules with high glass transition temperatures. These compounds have a number of qualities that make them useful in electroluminescence devices.

In one aspect, the present invention features substituted carbazole compounds of formula (I):

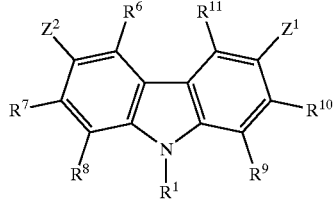

(I)

Each of $Z^1$ and $Z^2$, independently, is

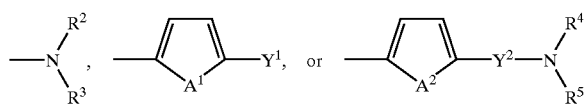

[referred to hereinafter as $N(R^2R^3)$, $A^1Y^1$, or $A^2Y^2N(R^4R^5)$]; each of $A^1$ and $A^2$, independently, is S, O, NR, or CH=CH; each of $Y^1$ and $Y^2$, independently, is aryl or heteroaryl; each of $R^1$–$R^5$, independently, is aryl or heteroaryl; and each of $R^6$–$R^{11}$, independently, is H, CN, alkyl, OR, NRR', COR, or C(O)OR; in which each of R and R', independently, is H or alkyl. Note that $Z^1$ and $Z^2$ can be two different $N(R^2R^3)$, two different $A^1Y^1$, or two different $A^2Y^2N(R^4R^4R^5)$.

Referring to formula (I), a subset of the carbazole compounds of this invention is featured by that each of $Z^1$ and $Z^2$, independently, is $N(R^2R^3)$. In these compounds, each of $R^6$–$R^{11}$ can be H; $R^1$ can be phenyl; each of $R^2$ and $R^3$, independently, can be aryl. In some embodiments, one of $R^2$ and $R^3$ is pyrenyl and the other is phenyl. Exemplary compounds include 9-N,N'-triphenyl-N,N'-di-pyren-1-yl-9H-carbazole-3,6-diamine (Compound 1), 9-phenyl-N,N'-di-pyren-1-yl-N,N'-di-p-tolyl-9H-carbazole-3,6-diamine (Compound 2), and N,N'-bis-(4-methoxy-phenyl)-9-phenyl-N,N'-di-pyren-1-yl-9H-carbazole-3,6-diamine (Compound 3).

Another subset of the carbazole compounds of this invention is featured by that each of $Z^1$ and $Z^2$, independently, is $A^2Y^2N(R^4R^5)$. In these compounds, $A^2$ can be S; each of $R^6$–$R^{11}$ can be H; $R^1$ can be phenyl; each of $R^4$ and $R^5$, independently, can be phenyl. In some embodiments, $Y^2$ is phenyl, carbazolyl, or fluorenyl. Exemplary compounds include 9-phenyl-3,6-bis{5-[4-diphenylamino-phenyl]-thiophen-2-yl}-9H-carbazole (Compound 4), 9-phenyl-3,6-bis{5-[3,5-bis(diphenylamino)-phenyl]-thiophen-2-yl}-9H-carbazole (Compound 5), 9-phenyl-3,6-bis[5-(3-diphenylamino-9-ethyl-carbazol-6-yl)-thiophen-2-yl]-9H-carbazole (Compound 6), or 9-phenyl-3,6-bis[5-(2-diphenylamino-9,9-diethyl-fluoren-7-yl)-thiophen-2-yl]-9H-carbazole (Compound 7).

Further, another subset of the carbazole compounds of this invention is featured by that each of $Z^1$ and $Z^2$, independently, is $A^1Y^1$. In these compounds, $A^1$ can be S; and $Y^1$ can be heteroaryl. An exemplary compound is 9-phenyl-3,6-bis[5-(carbazol-3-yl)-thiophen-2-yl]-9H-carbazole (Compound 8).

Still further another subset of the carbazole compounds of this invention is featured by that one of $Z^1$ and $Z^2$ is $N(R^2R^3)$ and the other is $A^1Y^1$.

In addition, salts of the carbazole compounds described above are within the scope of the invention. For example, a salt can be formed between a positively charged amino substituent and a negatively charged counterion.

Alkyl, aryl, heteroaryl, phenyl, pyrenyl, carbazolyl, and fluorenyl mentioned above include both substituted and unsubstituted moieties. The term "substituted" refers to one or more substituents (which may be the same or different), each replacing a hydrogen atom. Examples of substituents include, but are not limited to, halogen, amino, alkylamino, arylamino, dialkylamino, diarylamino, hydroxyl, mercapto, cyano, nitro, $C_1$~$C_6$ alkyl, $C_1$~$C_6$ alkenyl, $C_1$~$C_6$ alkoxy, aryl, heteroaryl, or heterocyclyl, wherein alkyl, alkenyl, alkoxy, aryl, heteroaryl, and heterocyclyl are optionally substituted with $C_1$~$C_6$ alkyl, halogen, amino, alkylamino, arylamino, dialkylamino, diarylamino, hydroxyl, mercapto, cyano, or nitro. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, pyridinyl, carbazolyl, and indolyl.

In another aspect, this invention features an electroluminescence device made with one or more of the carbazole compounds described above. The device includes a hole transporting layer, an emitting layer, and an electron transporting layer. The hole transporting layer, the emitting layer and the electron transporting layer are disposed in the above order, and at least one of the hole transporting layer and the emitting layer includes the carbazole compounds of this invention. In some embodiments, both the hole transporting layer and the emitting layer include the carbazole compounds.

The details of one or more embodiments of the invention are set forth in the description below. Other features, objects, and advantages of the invention will be apparent from the description and drawings, and from the claims.

DETAILED DESCRIPTION

The invention features carbazole compounds, and EL devices made using these compounds. In particular, the carbazole compounds are substituted at the 3-, 6-, and 9-positions. The substituted carbazoles improve the thermal stability and/or glassy state durability of organic compounds when incorporated into the cores of these compounds and are thus useful for making organic LEDs.

A method for synthesizing certain substituted carbazoles follows: A 9-substituted carbazole is prepared by coupling a carbazole with a halide in the presence of a catalyst. Examples of suitable halides include aryl halides and heteroaryl halides, in which the aryl groups may be substituted. Other examples of suitable halides include alkyl halides and vinyl halides. The result of the coupling reaction is a 9-substituted carbazole.

The 1, 2, 4, 5, 7, and 8-positions of the starting carbazole may be H, or they may be CN, allyl, OR, NRR', COR, or C(O)OR; wherein each of R and R', independently, is H or alkyl. Thus, other positions of the carbazole may be substituted; however, the product of the coupling reaction will be referred to simply as a "9-substituted carbazole" for brevity.

The 9-substituted carbazole is converted to a 9-substituted, 3,6-dihalocarbazole by treating the 9-substituted carbazole with a halogenating agent. The 9-substituted, 3,6-dihalocarbazole is converted to a 9-substituted, 3,6-diaminocarbazole by coupling the dihalo compound with an amine, or a mixture of amines in presence of a catalyst, such as a catalyst developed by Koie (Nishiyama et al. (1998) *Tetrahedron Lett.* 39: 617), or Hartwig (Hartwig et al. (1999) *J. Org. Chem.* 64: 5575). The catalyst shown in Scheme 1, Pd(dba)$_2$ (dba= dibenzylideneacetone)/P(t-Bu)$_3$, in the presence of NaO-t-Bu, can efficiently catalyze C—N bond formation between an aryl halide and an aryl amine Secondary amines are preferred in the just-described reaction; the amines can be symmetrical or asymmetric. The amines can have saturated or unsaturated aliphatic substituents, or aromatic substituents, with aromatic substituents, especially fused aromatic substituents, being preferred. The aliphatic or aromatic substituents can in turn be substituted with various functional groups, including both electron-donating groups and electron-withdrawing groups. The secondary amines can be prepared by coupling primary amines with halides in the presence of a catalyst.

Shown below is a scheme (Scheme 1) that depicts synthesis of Compounds 1–3.

Scheme 1

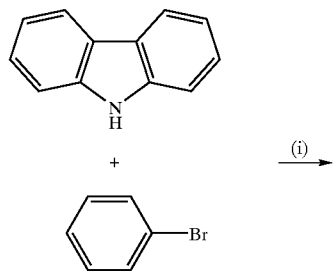

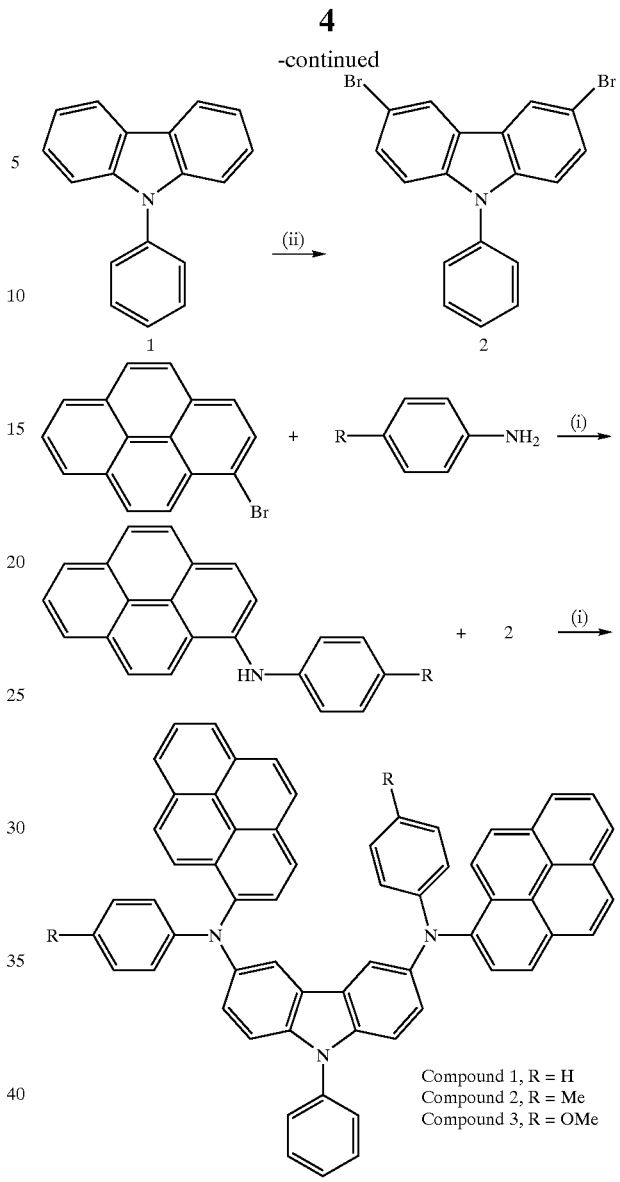

(i) 2 mol % Pd(dba)$_2$, 2–3 mol % P(t-Bu)$_3$ (1.5 equiv.)
NaO-t-Bu, toluene, 6 h at 80° C. or 12 h at r.t.
(ii) NBS, DMF, 0° C.

A method for synthesizing other substituted carbazoles follows: A 9-substituted, 3,6-dihalocarbazole is obtained by the method described above. The 9-substituted, 3,6-dihalocarbazole can be converted to a 9-substituted, 3,6-thiophene-substituted triarylamines by coupling the dihalo compound with a thiophene-substituted triarylamine intermediate. The intermediate can be prepared through two different routes (Scheme 2). In route A, an aromatic dihalide is monothienylated by a Stille coupling reaction with thienyl tri-n-butyl stannane, followed by a C—N coupling reaction with diarylamine to produce the desired intermediate. Alternatively (route B), a triarylamine is first monobrominated by, e.g., NBS/DMF, followed by palldium(0) catalyzed corss-coupling of the bromo derivative with thienyl tri-n-butyl stannane to form a thienyl-triarylamine congener. The thiophene derivative is conveniently converted into the required stannanes by a procedure involving lithiation followed by quenching with tri-n-butyl tin chloride. See, for example, Wu et al. (2000) *Adv. Mater.* 12: 668 and Wu et al. (1999) *J. Am. Chem. Soc.* 121: 472.

Scheme 2

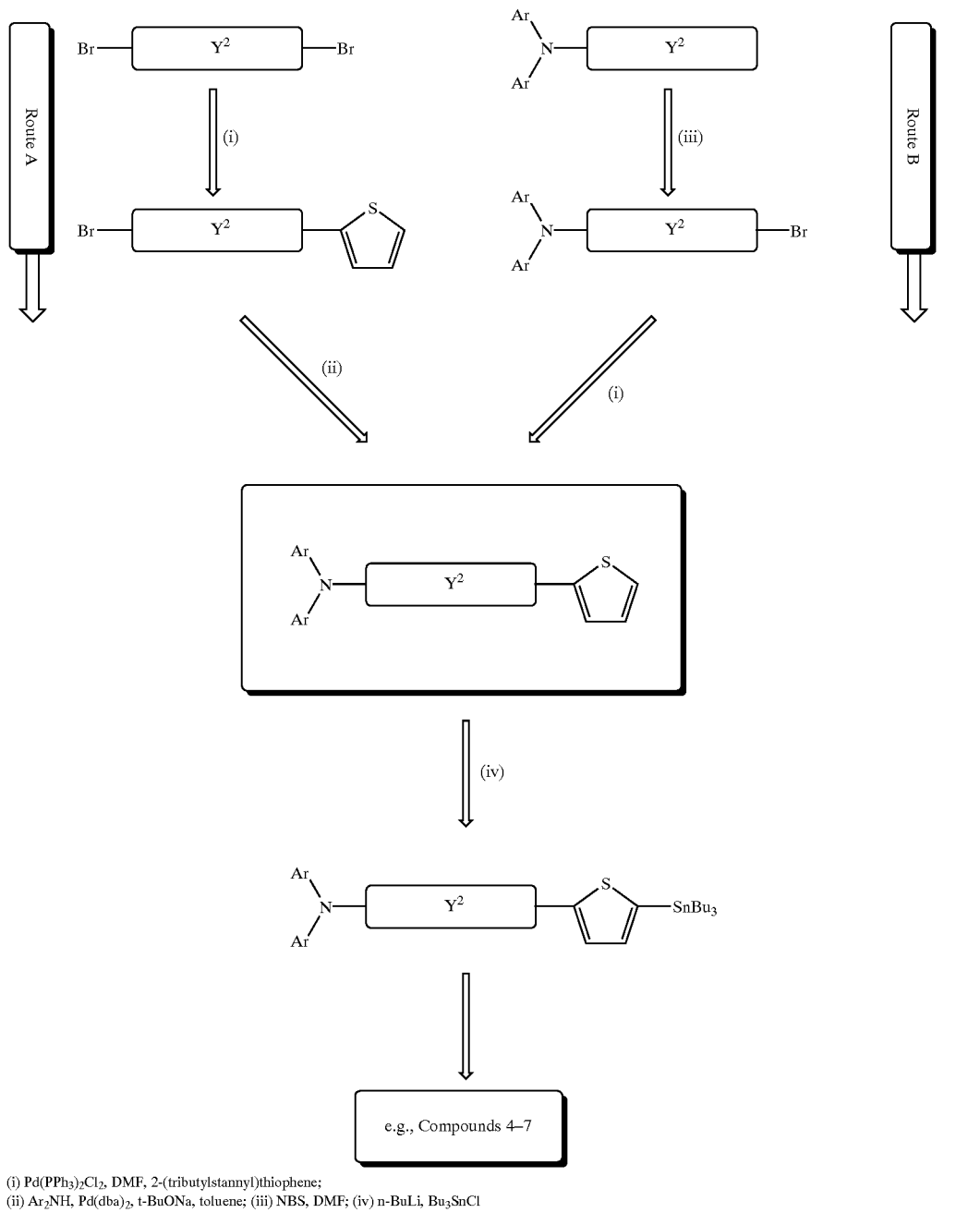

(i) Pd(PPh$_3$)$_2$Cl$_2$, DMF, 2-(tributylstannyl)thiophene;
(ii) Ar$_2$NH, Pd(dba)$_2$, t-BuONa, toluene; (iii) NBS, DMF; (iv) n-BuLi, Bu$_3$SnCl The thiophene shown in Scheme 2 can be replaced by furan, pyrrole, or benzene. The 3- or 6-position of carbazole can also be substituted with an oligo-aryl chain, such as the carbazol-thiophen present in Compound 8.

The compounds of the invention can be used to make EL devices. A diagrammatic representation of such a device is shown below:

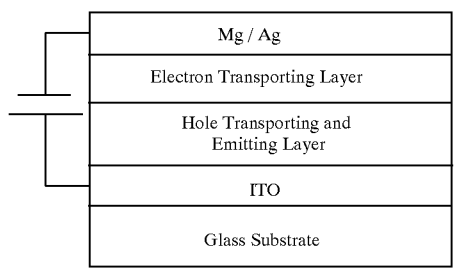

Electroluminescence devices generally include multiple layers. A typical device includes a substrate (e.g., glass), which may be coated with an oxide. The device also includes a hole transporting layer, an electron transporting layer, and an emitting layer. The hole transporting layer and the emitting layer may be combined into a single layer, or the emitting layer and the electron transporting layer may be combined into a single layer. The devices may also include a cathode.

The compounds of the invention can be used in the hole-transporting layer, the emitting layer, or in both layers.

Without further elaboration, it is believed that one skilled in the art can, based on the description herein, utilize the present invention to its fullest extent. All publications recited herein are hereby incorporated by reference in their entirety. The following specific examples, which describe the synthesis of various compounds of the invention, are therefore to be construed as merely illustrative, and not limitative of the remainder of the disclosure in any way.

EXAMPLE 1

Synthesis of Compound 1: 9-N,N'-triphenyl-N,N'-di-pyren-1-yl-9H-carbazole-3,6-diamine 1-Bromopyrene (10 mmol), $C_6H_5NH_2$ (12 mmol), $Pd(dba)_2$ (0.20 mmol), $P(t-Bu)_3$ (0.20–0.30 mmol) and sodium t-butoxide (1.44 g, 15 mmol) were charged in a two-necked flask under a nitrogen atmosphere. Toluene (25 ml) was added and the resulting violet solution was stirred at room temperature for 8 hours. During this period the contents of the flask became a pale yellow fluorescent solution. The reaction was quenched with water (30 ml) and the organic layer was taken into 100 ml diethyl ether, washed with brine solution, and dried over $MgSO_4$. Evaporation of the solvent under vacuum resulted in a yellow solid that was adsorbed in silica gel and purified by column chromatography using dichloromethane/hexane (1:1) as eluant to produce phenyl-pyren-1-yl-amine (89%).

$^1$H NMR(300 MHz, acetone-$d_6$, TMS): $\delta$[ppm]= 6.87–6.92(m, 1 H), 7.17–7.20(m, 2 H), 7.24–7.30(m, 2 H), 7.96–8.09(m, 5 H), 8.15–8.20(m, 3 H), 8.37(d, 9.4 Hz, 1 H); MS (FAB): m/z 293 ($M^+$, 100%).

3,6-Dibromo-N-phenyl-carbazole (1 mmol), phenyl-pyren-1-yl-amine (2.1 mmol), $Pd(dba)_2$ (0.04 mmol), $P(t-Bu)_3$ (0.04–0.06 mmol), sodium t-butoxide (0.288 g, 3 mmol), and toluene (20 ml) were mixed together and heated at 80° C. for 4–6 hours. The reaction was quenched with water (30 ml) and the organic layer was taken into 100 ml diethyl ether, washed with brine solution and dried over $MgSO_4$. Evaporation of the solvent under vacuum resulted in a yellow solid that was adsorbed in silica gel and purified by column chromatography using dichloromethane/hexane mixture as eluant to produce Compound 1 (94%).

$^1$H NMR(300 MHz, $CDCl_3$, TMS): $\delta$[ppm]=6.78–6.87(m, 6 H), 7.08(t, 4 H, J=7.6 Hz), 7.25(d, 6 H, J=5.8 Hz), 7.36–7.42(m, 1 H), 7.51–7.54(m, 2 H), 7.76–7.80(m, 4 H), 7.86(d, 2 H, J=9.1 Hz), 7.93(t, 2 H, 7.4 Hz), 7.98(s, 4 H), 8.03–8.10(m, 6 H), 8.19(d, 2 H, J=9.3 Hz); MS (FAB): m/z 825($M^+$, 100%); elemental analyses: calculated: C 90.15, H 4.76, N 5.09; found: C 90.34, H 4.60, N 5.01.

EXAMPLE 2

Synthesis of Compound 2: 9-Phenyl-N,N'-di-pyren-1-yl-N,N'-di-p-tolyl-9H-carbazole-3,6-diamine Compound 2 was prepared in a similar manner (yield 85%) as described in Example 1.

$^1$H NMR(300 MHz, $CDCl_3$, TMS): $\delta$[ppm]=2.21(s, 6 H), 6.80(d, 4 H, J–8.3 Hz), 6.91(d, 4 H, J=8.4 Hz), 7.16–7.25(m, 4 H), 7.34–7.41(m, 1 H), 7.53(d, 4 H, J=4.3 Hz), 7.71–7.77 (m, 4 H), 7.84(d, 2 H, J=9.3 Hz), 7.91(d, 2 H, J=7.4 Hz), 7.97(s, 4 H), 8.02–8.11(m, 6 H), 8.18(d, 2 H, J=9.4 Hz); MS (FAB): m/z 853($M^+$, 100%); elemental analyses: calculated: C 90.01, H 5.07, N 4.92; found: C 89.91, H, 5.21, N 5.10.

EXAMPLE 3

Synthesis of Compound 3: N,N'-Bis-(4-methoxy-phenyl)-9-phenyl-N,N'-di-pyren-1-yl-9H-carbazole-3,6-diamine Compound 3 was prepared in a similar manner (yield 89%) as described in Example 1.

$^1$H NMR(300 MHz, $CDCl_3$, TMS): $\delta$[ppm]=3.7(s, 6 H), 6.66–6.70(m, 4 H), 6.87–6.91(m, 4 H), 7.11(dd, 2 H, J=6.7, 2.1 Hz), 7.22(d, 2 H, J=8.2 Hz), 7.35–7.40(m, 1 H), 7.52(d, 4 H, J=4.4 Hz), 7.63(d, 2 H, J=1.9 Hz), 7.71(d, 2 H, J=8.2 Hz), 7.82(d, 2 H, J=9.3 Hz), 7.91(t, 2 H, J=7.5 Hz), 7.96(s, 4 H), 8.01–8.10(m, 6 H), 8.17(d, 2 H, J=9.4 Hz,); MS (FAB): m/z 885($M^+$, 100%); elemental analyses: calculated: C 86.75, H 4.89, N 4.74; found: C 86.67, H 4.92, N 4.65.

EXAMPLE 4

Synthesis of Compound 4: 9-phenyl-3,6-bis{5-[4-diphenylamino-phenyl]-thiophen-2-yl}-9H-carbazole A Schlenk tube was charged with 3,6-dibromo-N-phenyl-carbazole (401 mg, 1 mmol), 4-(5-tributylstannyl-2-thienyl)triphenylamine (1.36 g, 2.2 mmol) $Pd(PPh_3)_2Cl_2$ (14 mg, 0.002 mmol) and 10 mL dimethyl formamide and heated at 60–70° C. for 18 h. The reaction was quenched by the addition of methanol and the yellow precipitate formed was collected by filtration. It was dissolved in dichlomethane and purified by column chromatography on silica gel. The second yellow band contained Compound 4 in 76% (680 mg) yield.

$^1$H NMR ($CDCl_3$, $\delta$): 7.00–7.14 (m, 18 H), 7.25–7.30 (m, 9 H), 7.37 (d, J=8.5 Hz, 2 H), 7.44–7.54 (m, 6 H), 7.56–7.69 (m, 6 H), 8.38 (d, J=1.2 Hz, 2 H). $^{13}$C NMR ($CDCl_3$, $\delta$): 110.3, 117.5, 123.0, 123.2, 123.8, 124.5, 126.3, 127.0, 127.7, 129.3, 130.0, 140.8, and 147.1. FAB mass (m/z): 893 ($M^+$). Anal. Calcd for $C_{62}H_{43}N_3S_2$: C, 83.28; H, 4.85; N, 4.70. Found: C, 83.02; H, 4.84; N, 4.62.

EXAMPLE 5

Physical Properties of Compounds 1–8

Compounds 1–8 had high decomposition temperatures; compositions made with these compounds therefore have good thermal stability. It is likely that the presence of fused aromatic substituents contributed to thermal stability. In addition, these compounds also had high glass transition temperatures ($T_g$), as shown in Table 1 and 2, which may provide for improved lifetimes in devices.

EXAMPLE 6

Electronic Properties of Compounds 1–8

Electrochemical characteristics of the carbazole compounds of this invention were investigated by using cyclic and differential pulse voltammetric methods.

For Compounds 1–3, cyclic voltammograms of these compounds in $CH_2Cl_2$ containing 0.1 M TBAP at 25° C. were determined, and showed that the first oxidation occurred readily; which could be due to the electron-donating nature of the carbazole segment. The oxidation of these carbazoles was irreversible, and was mainly destabilized by the two cation radicals formed from the peripheral amines. The fourth wave showed in volatmmogram indicated the formation of the dication radical. In Compound 3, four reversible waves were detected. The first two low-oxidation potentials originated from the peripheral amines, and the first high oxidation potential originated from the carbazole core. The influence of peripheral amines on the carbazole core was evident, as the oxidation potential of the carbazole core decreases (Compound 1>Compound 2>Compound 3) with increasing electron donating ability of R (H<Me<OMe) in the peripheral amines. In addition, Compounds 1–3 are green light emitters both in solution and in the solid state. The solution ($CH_2Cl_2$) fluorescence quantum yields were found to be 0.12, 0.11, and 0.19, respectively, for Compound 1, Compound 2, and Compound 3.

For Compounds 4–8, the emission spectra in solution displayed vibronic strictures. In the condensed state, the vibronic structures in the emission were dramatically reduced for these compounds. This meant that the amorphism was enhanced in the solid state. These compounds underwent a prominent red shift in their emission at the filmy state. Cyclic and differential pulse voltammetric methods were used to determine the HOMO energy levels. Ferrocene served as an internal standard for calibrating the potential and calculating the HOMO levels (−4.8 eV). The pertinent data are listed in Table 2.

In general, these compounds undergo a reversible multi-electron (two or three) oxidation arising from terminal diphenylamino units followed by a series of reversible or irreversible oxidations originating from bridging aromatic segments. The reversibility of the latter oxidations is largely governed by the spacers (i.e., $Y^2$). A carbazole conjugated compound (e.g., Compound 4 or 7) displayed two or three reversible oxidations. The first two-electron wave was assigned to the simultaneous oxidation of the peripheral diphenylamino units while the next two one-electron oxidations stemed from thiophene and carbazole cores. A reversible thiophene based redox couple was located ca. +400 mV vs $Fc/Fc^+$ when it was placed in between two efficient donors. Alternatively a carbazole conjugated analog (e.g., Compound 6) exhibited two reversible oxidations originating from diphenylamino and carbazole/thiophene segments. Thus, carbazole being sufficiently electron-rich pushed electron density towards the diphenylamino group and made it lose electrons relatively facile. This order is perturbed slightly in carbazole based derivatives: Compound 5>Compound 7>Compound 4>Compound 6≈Compound 8, due to the additional charge donation from carbazole core that is effectively transmitted to the peripheral diphenylamine segment if the spacer is short.

EXAMPLE 6
LEDs Fabrication and Measurement.

EL devices using the carbazole compounds of this invention as the hole-transporting layer as well as the emitting layer and TPBI (1,3,5-tris(N-phenylbezimidazol-2-yl) benzene) or $Alq_3$ (tris(8-hydroxyquinoline) aluminum) as the electron transporting layer were fabricated. See, for example, Gao et al. (1999) *Appl. Phys. Lett.* 74: 865; and Zhang et al. (2000) *Chem. Phys. Lett.* 320: 77. Take Compound 1 as an example. A device was prepared by vacuum deposition of 400 Å of Compound 1, followed by 400 Å of $Alq_3$ ($Alq_3$=tris(8-quinolinolato)aluminum (III), See, e.g., Tang & VanSlyke (1987) *Appl. Phys. Lett.* 51: 913; and Kido & Lizumi (1997) *Chem. Lett.* 963) onto an indium-tin-oxide (ITO) coated glass substrate. The deposition rate was 2–5 Å/s at $2 \times 10^{-5}$ Torr. An alloy of magnesium and silver (ca. 8:1, 500 Å), which served as the cathode, was deposited onto the organic layer by simultaneously evaporating from two different sources. The cathode was capped with 1000 Å of silver.

The current-voltage (I-V) curve was measured on a Keithley 2000 Source Meter in an ambient environment. Light intensity (L) was measured with a Newport 1835 Optical Meter.

The I-V-L characteristics of a device made with Compound 1 was determined. The device was ITO/Compound 1/TPBI/Mg:Ag. Green light emission from Compound 1 at 530 nm was observed. The green emission confirms the role of TPBI in confining the charge recombination in the hole-transporting layer (HTL). While the device is not optimized, the physical performance appears to be promising; the device has a turn on voltage of 5 V, a maximum luminescence of 38000 $cd/m^2$ at 13.5 V, external quantum efficiency of 1.5% at 5 V, and luminous efficiency of 2.5 lm/W at 5 V The characteristics of devices made with Compounds 4, 5, 6, and 8 were also determined. Two types of double-layer EL devices (ITO/Compound/TPBI/Mg:Ag and ITO/Compound/$Alq_3$/Mg:Ag) used these compounds as hole transporting layer and $Alq_3$ or TPBI as electron transporting layer. These devices were prepared by vacuum deposition of 400 Å of the hole transporting layer, followed by 400 Å of TPBI or $Alq_3$. An alloy of magnesium and silver (ca. 10:1, 500 Å) was deposited as the cathode, which was capped with 1000 Å of silver. The salient parameters are compiled in Tables 3. All these devices in this study exhibited a relatively low turn-on voltages (2.5–3.0 V) and operating voltages (5.6–7.2 V at a current density of 100 $mA/cm^2$). For comparison, a typical device using NPD (1,4-bis(1-naphthylphenylamino)biphenyl) as the hole transporting layer was also prepared.

It is interesting to note that the devices including Compound 4 or 5 emited pure blue light based on their Commission Internationale d'Eclairage (CIE) chromaticity coordinates ((x, y): Compound 4, (0.17, 0.20); Compound 5, (0.14, 0.14)). The physical performance for the devices (brightness, external quantum efficiencies, and luminous efficiencies at a current density of 100 $mA/cm^2$) appears to be promising (Compound 4: 2375 $Cd/m^2$, 1.67%, 1.10 lm/W; Compound 5: 2121 $Cd/m^2$, 1.73%, 1.10 lm/W) when compared to the blue-emitting devices reported recently. See, for example, Hosokawa et al. (1995) *Appl. Phys. Lett.* 67: 3853; Gao et al. (1999) *Appl. Phys. Lett.* 74: 865; Balasubramaniam et al. (2000) *Chem. Mater.* 12: 2788; Leung et al. (2000) *J. Am. Chem. Soc.* 122: 5640; Tao et al. (2001) *Chem. Maier.* 13: 1207; and Ko et al. (2001) *Chem. Mater.* 13: 2441.

Differential scanning calorimetry (DSC) measurements were carried out using a Perkin Elmer 7 series thermal analyzer at a heating rate of 10 degree/minute. TGA measurements were performed on a Perkin Elmer TGA7 thermal analyzer using $O_2$ as carrier gas. Electronic absorption spectra were obtained on a Perkin-Elmer Lambda 9 spectrometer. Cyclic voltammetry (CV) and Osteroung square wave voltammetry (ferrocene as internal standard) measurements were carried out in a three electrode and potentiostat configuration on a Bioanalytical System BAS 100B.

TABLE 1

Physical Data for Compounds 1–3

| Compound | $T_g/T_m$ [a] | $T_d$ [b] | $\lambda_{max}$ [c] | $\lambda_{em}$ ($\Phi_f$) [d] | $E_{ox}$ ($\Delta E_p$) [e] |
|---|---|---|---|---|---|
| 1 | 180/355 | 463 | 408, 318, 274 | 535 (0.12) | 167 (74), 457 (69), 1002 (i) |
| 2 | 184/NA[a] | 513 | 415, 319, 274 | 543 (0.11) | 111 (71), 511 (73), 818 (76), 986 (i) |
| 3 | 183/NA[a] | 455 | 420, 319, 274 | 553 (0.19) | 63 (77), 348 (72), 769 (63), 885 (75) |

[a]° C., obtained from DSC measurements; NA: $T_m$ not detected. [b] ° C., obtained from TGA measurements. [c]nm, measured in $CH_2Cl_2$ solution; [d]nm, measured in $CH_2Cl_2$ solution; Φf: fluorescence quantum efficiency; [e]mV, measured in $CH_2Cl_2$. All $E_{ox}$ data are reported relative to ferrocene which has an $E_{ox}$ at 226 mV relative to Ag/Ag$^+$and the anodic peak-cathodic peak separation ($\Delta E_p$)is 90 mV, I = irreversible process. The concentration of the complexes used in this experiment was $2.5 \times 10^{-4}$ M and the scan rate was 100 mV s$^{-1}$.

TABLE 2

Physical Data for Compounds 4–8

| Compound | $T_g$ [a] | $T_d$ [b] | $\lambda_{max}$ [c] | $\lambda_{em}$ ($\Phi_f$) [d] | $\lambda_{em}$ [e] | $E_{ox}$ ($\Delta E_p$) [f] | HOMO/LUMO [g] |
|---|---|---|---|---|---|---|---|
| 4 | 128 | 545 | 376 (75.1), 308 (38.9) | 462,441 (0.51) | 486 | 313 (95), 562 (64), 823 (62) | 5.113/2.293 |
| 5 | 146 | 560 | 321 (237.2) | 427,441 (0.21) | 473, 494 | +462 (135) | 5.262/2.308 |
| 6 | 178 | 534 | 355 (85.3), 313 (79.1) | 451,431 (0.26) | 506 | 205 (83), 489 (86) | 5.008/2.122 |
| 7 | 156 | 524 | 394 (106.6), 315 (39.05) | 450, 473 (0.31) | 496 | +321 (79), 472 (71), 671 (60) | 5.12 1/2.364 |
| 8 | 142 | 580 | 348 (119.6) | 421,445 (0.27) | 513 | +203 (124) | 5.003/2.083 |
| TPD | | | | | | | 4.70 (EF)/na |
| TPBI | | | | | | | 6.20/2.70 |
| Alq3 | | | | | | | 6.09/2.95 |
| Mg:Ag | | | | | | | na/3.70 ($E_F$) |

[a]° C., obtained from DSC measurements. [b]° C., obtained from TGA measurements. [c] $\epsilon_{max} \times 10^{-3}$) nm, measured in a $CH_2Cl_2$ solution, $\epsilon_{max}$ in M$^{-1}$ cm$^{-1}$ in parentheses. [d] nm, measured in a $CH_2Cl_2$ solution; $\phi_f$ fluorescence quantum yield. [e] nm, film samples. [f] mV, measured in $CH_2Cl_2$. All $E_{ox}$ data are reported relative to ferrocene, which has an $E_{ox}$ at 223 mV relative to Ag/Ag+ and the anodic peak-cathodic peak separation ($\Delta E_p$) is 75 mV. The concentration of the compounds used in this experiment was $2.5 \times 10^{-4}$ M and the scan rate was 100 mV s$^{-1}$. [g] na, not available.

TABLE 3

Electroluminescence data for some compounds

| | Compound 4 [a] TPBI/Alq$_3$ | Compound 5 [a] TPBI/Alq$_3$ | Compound 6 [a] TPBI/Alq$_3$ | Compound 8 [a] TPBI/Alq$_3$ |
|---|---|---|---|---|
| turn-on voltage, V | 2.7/3.0 | 3.0/2.0 | 2.5/2.5 | 3.0/3.0 |
| max brightness, Cd/m$^2$ | 19944/21330 | 10502/40215 | 20760/18500 | 20763/17270 |
| max external quantum effic, % | 1.67/0.76 | 1.78/1.50 | 1.30/0.66 | 1.30/0.66 |
| max power effic, lm/W | 1.41/1.70 | 2.00/3.07 | 2.05/1.31 | 1.25/0.96 |
| $\lambda_{em}$ | 474/522 | 458/522 | 485/522 | 470/522 |
| CIE, x, y | 0.17, 0.20/ 0.31, 0.53 | 0.14, 0.14/ 0.31, 0.56 | 0.17, 0.25/ 0.31/ 0.53 | 0.17, 0.25/ 0.27, 0.53 |
| Voltage [b], V | 6.7/7.3 | 6.0/6.9 | 6.5/6.8 | 5.6/6.6 |
| Brightness [b], Cd/m$^2$ | 2375/2305 | 2121/4395 | 1521/1544 | 2231/2026 |
| external quantum effic, $^c$ % | 1.67/0.75 | 1.73/1.47 | 0.70/0.56 | 1.28/0.66 |
| power effic, $^c$ lm/W | 1.10/0.99 | 1.10/2.25 | 0.73/0.71 | 1.25/0.96 |

[a] ITO/Compound (400 Å)/TPBI (400 Å)/Mg:Ag. [b] Taken at a current density of 100 mA/cm$^2$.

Other Embodiments

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Accordingly, other embodiments are also within the scope of the following claims.

What is claimed is:

1. A compound of formula (I):

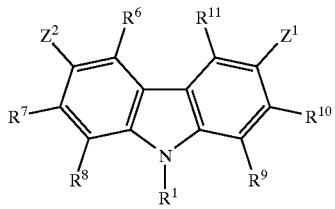

(I)

wherein each of $Z^1$ and $Z^2$, independently, is;

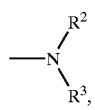

$R^1$ is heteroaryl or unsubstituted aryl;
each of $R^2$–$R^3$, independently, is aryl or heteroaryl; and
each of $R^6$–$R^{11}$, independently, is H, CN, alkyl, OR, NRR', COR, or C(O)OR; and
each of R and R', independently, is H or alkyl.

2. The compound of claim 1, wherein each of $R^6$–$R^{11}$ is H.

3. The compound of claim 2, wherein $R^1$ is phenyl.

4. The compound of claim 3, wherein each of $R^2$ and $R^3$, independently, is aryl.

5. The compound of claim 4 wherein one of $R^2$ and $R^3$ is pyrenyl.

6. The compound of claim 5, wherein the other of $R^2$ and $R^3$ is phenyl.

7. The compound of claim 5, wherein the compound is 9-N,N'-triphenyl-N,N'-pyren-1-yl-9H-carbazole-3,6-diamine, 9-phenyl-N,N'-di-pyren-1-yl-N,N'-di-p-tolyl-9H-carbazole-3,6-diamine, or N,N'-bis-(4-methoxy-phenyl)-9-phenyl-N,N'-di-pyren-1-yl-9H-carbazole-3,6-diamine.

8. The compound of claim 1, wherein $R^1$ is phenyl.

9. The compound of claim 8, wherein each of $R^2$ and $R^3$, independently, is aryl.

* * * * *